United States Patent [19]
Nagel et al.

[11] Patent Number: 5,948,631
[45] Date of Patent: Sep. 7, 1999

[54] STABLE MIXTURE FOR THE DETECTION OF ALKALINE PHOSPHATASE CONTAINING A SALT OF O-CRESOLPHTHALEIN MONOPHOSPHORIC ACID

[75] Inventors: Rolf Nagel, Bürstadt; Steffen Bossert-Reuther, Heidelberg; Thomas Zeibig, Dannstadt-Schauernheim, all of Germany

[73] Assignee: Roche Diagnostics GmbH, Mannheim, Germany

[21] Appl. No.: 08/924,480

[22] Filed: Aug. 7, 1997

[30] Foreign Application Priority Data

Aug. 12, 1996 [DE] Germany .......................... 196 32 432

[51] Int. Cl.$^6$ ............................ C12Q 1/42; G01N 31/22; G01N 21/78; C07F 9/06
[52] U.S. Cl. .......................... 435/21; 435/287.7; 436/169; 549/220
[58] Field of Search ................................. 435/21, 287.7; 436/169; 549/220

[56] References Cited

U.S. PATENT DOCUMENTS

| | | | |
|---|---|---|---|
| 3,975,405 | 8/1976 | Hamill | 549/220 |
| 4,900,665 | 2/1990 | Terashima et al. | 435/21 |
| 4,985,414 | 1/1991 | Guethlein et al. | 514/100 |
| 5,211,914 | 5/1993 | Vogel et al. | 422/56 |

FOREIGN PATENT DOCUMENTS 0 182 179  10/1989  European Pat. Off. .

*Primary Examiner*—Kathleen K. Fonda
*Assistant Examiner*—Marjorie A. Moran
*Attorney, Agent, or Firm*—Nikaido Marmelstein Murray & Oram, LLP.

[57] ABSTRACT

The subject matter of the invention is a stable mixture for the detection of alkaline phosphatase, wherein it contains the N-methylglucamine salt of o-cresolphthalein monophosphoric acid and N-methylglucamine as well as an analytical element for the detection of alkaline phosphatase with a matrix that carries this mixture. In addition the invention concerns a method for the determination of alkaline phosphatase using a salt of o-cresolphthalein monophosphoric acid, wherein the sample is brought into contact with a mixture according to the invention or an analytical element according to the invention and a change in color is observed in the presence of alkaline phosphatase.

A subject matter of the invention is also a salt of o-cresolphthalein monophosphoric acid with N-methylglucamine as well as a process for producing such a salt.

32 Claims, 1 Drawing Sheet

STABLE MIXTURE FOR THE DETECTION OF ALKALINE PHOSPHATASE CONTAINING A SALT OF O-CRESOLPHTHALEIN MONOPHOSPHORIC ACID

The invention concerns a stable mixture for the detection of alkaline phosphatase containing a salt of o-cresolphthalein monophosphoric acid. The invention also concerns an analytical element for the detection of alkaline phosphatase containing a matrix which contains a substrate for the enzyme alkaline phosphatase which leads to a colour change in the presence of the enzyme. A further subject matter of the invention is a method for the determination of alkaline phosphatase using a salt of o-cresolphthalein monophosphoric acid as an enzyme substrate and a phosphoric acid acceptor. Finally a subject matter of the invention is also a salt of o-cresolphthalein monophosphoric acid with N-methylglucamine and a process for the production of such a salt.

The determination of the alkaline phosphatase activity in human body fluid is clinically very important. The U.S. Pat. No. 3,975,405 describes the use of o-cresolphthalein monophosphoric acid salts as substrates for the determination of alkaline phosphatase. Alkaline, alkaline earth and ammonium salts as well as salts of protonated organic amines are mentioned as preferred salts. Examples of such protonated organic amines are cyclohexylammonium, tetramethylethylene diammonium and ethanolammonium. In order to carry out an alkaline phosphatase test in blood serum o-cresolphthalein monophosphate disodium salt is used together with diethanolamine as a phosphoric acid acceptor which is present at a very high concentration (one molar) as a buffer containing magnesium chloride. However, this o-cresolphthalein monophosphoric acid salt is not stable towards non-enzymatic hydrolysis. This means that o-cresolphthalein monophosphate is converted and colour is formed even in the absence of the enzyme to be determined. The sensitivity of the alkaline phosphatase test is reduced because the measurement has to be carried out in the presence of an increased colour background or the presence of enzyme which is not actually present is even simulated.

This problem is addressed in the European Patent Application 0182179. It recommends that the enzyme substrate and phosphoric acid acceptor are spatially separated before carrying out the test in order to increase the stability of the detection reagents for alkaline phosphatase and only to bring both of them into contact together with the sample liquid to be examined. A multi-layered analytical element is described for this in which the substrate for alkaline phosphatase and the phosphoric acid acceptor are on different layers. Aryl phosphate ammonium salts are mentioned as possible alkaline phosphatase substrates in which the aryl group can be nitro-substituted phenyl, phenolphthalein, thymolphthalein, arylazo-substituted aryl or fluorescein and the ammonium group can be N-methylglucamine among others. Amino alcohols which also include N-methylglucamine are stated as preferred phosphoric acid acceptors. o-Cresolphthalein monophosphates are not stated as possible phosphatase substrates. A major disadvantage of the subject matter of the European Patent Application 0182179 is the separation of substrate and phosphoric acid acceptor. The application of the respective substances to separate layers of an analytical element complicates the construction of the test strip. Furthermore it must be taken into consideration that each layer absorbs sample liquid volume. However, when analytical elements are used the amount of sample liquid which is available is often very small and scarce. In addition when liquid sample is applied to the separated substrate and acceptor layers problems with the homogeneous mixing of substrate, phosphoric acid acceptor and sample can occur which may lead to a considerable scattering of the measured values.

Therefore the object of the present invention was to avoid the disadvantages of the state of the art.

This is achieved by the subject matter of the invention as characterized in the claims.

A subject matter of the invention is a stable mixture for the detection of alkaline phosphatase which contains the N-methylglucamine salt of o-cresolphthalein monophosphoric acid as the enzyme substrate and N-methylglucamine as the phosphoric acid acceptor. Both are preferably present together in a homogeneous mixture.

The invention also concerns an analytical element for the detection of alkaline phosphatase preferably in a liquid sample containing a matrix which contains a substrate for the enzyme alkaline phosphatase which leads to a change in colour in the presence of the enzyme wherein the matrix carries the said mixture according to the invention and thus the enzyme substrate as well as the phosphoric acid acceptor are present in or on one layer.

A further subject matter of the invention is a method for the determination of alkaline phosphatase using a salt of o-cresolphthalein monophosphoric acid as the enzyme substrate and a phosphoric acid acceptor wherein the sample to be examined is contacted with a mixture according to the invention or an analytical element according to the invention and a change in colour is observed when alkaline phosphatase is present.

The salt of o-cresolphthalein monophosphoric acid with N-methylglucamine is new and is therefore also a subject matter of the invention as is the process for the production of such a salt from o-cresolphthalein monophosphoric acid and N-methylglucamine.

Figure 1:
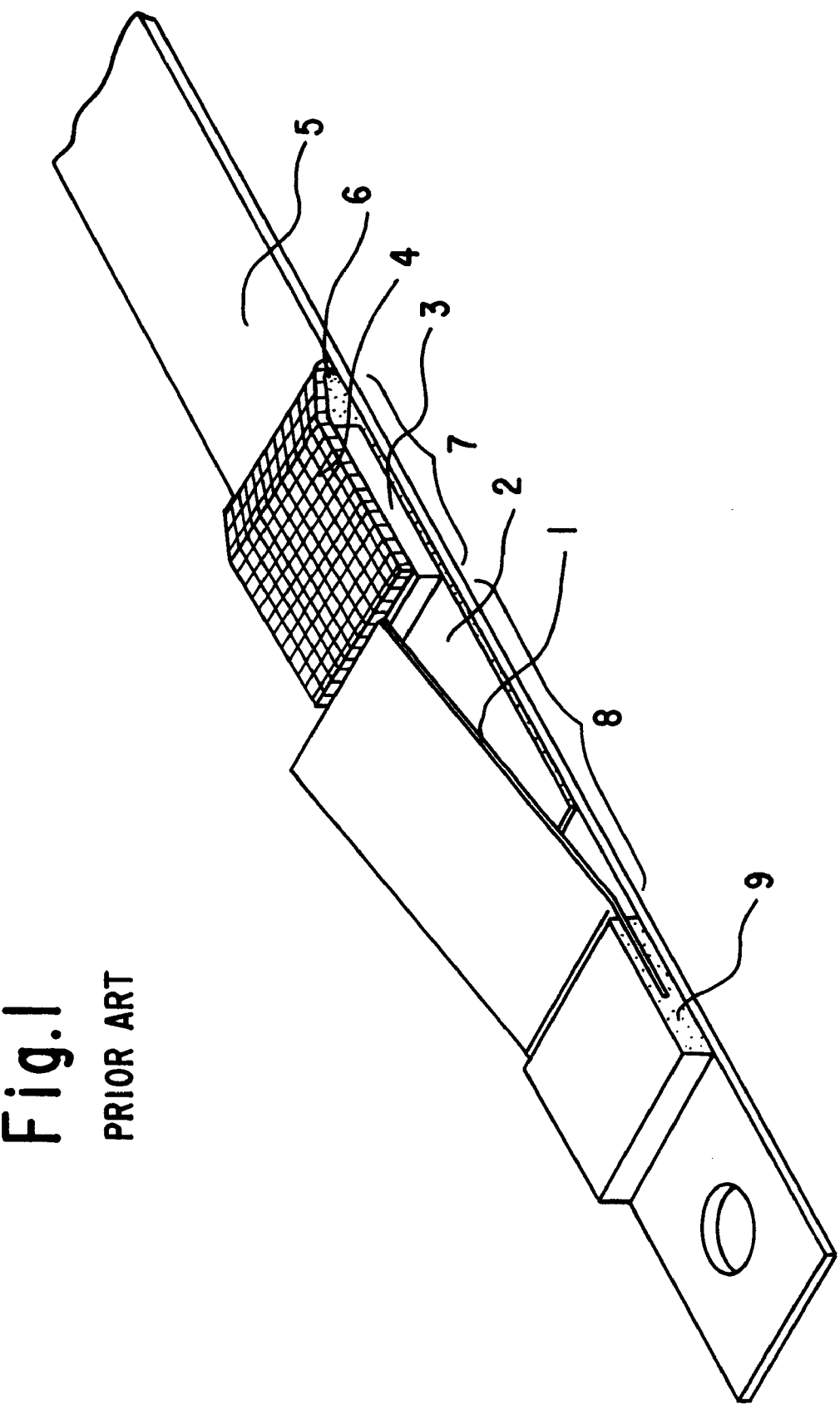
FIG. 1 shows a prior art analytical element.

It has surprisingly turned out that a mixture of the N-methylglucamine salt of o-cresolphthalein monophosphoric acid and additional N-methylglucamine as a phosphoric acid acceptor can be used to determine alkaline phosphatase and is very stable towards non-enzymatic hydrolysis. This also applies when the mixture contains buffer substance and all other substances required for the alkaline phosphatase test. The presence of buffer substance or phosphoric acid acceptor especially has been regarded in the European Patent Application 0182179 as being a major cause of the non-enzymatic hydrolysis of substrates of the enzyme alkaline phosphatase. The D-N-methylglucamine salt is advantageously used as the N-methylglucamine salt of o-cresolphthalein monophosphoric acid and preferably free, i.e. additionally added, D-N-methylglucamine is used as the phosphoric acid acceptor. The salt of o-cresolphthalein monophosphoric acid can contain 1 to 3 N-methylglucammonium ions per o-cresolphthalein monophosphate molecule. The o-cresolphthalein monophosphate of the present invention preferably contains 2 to 3 N-methylglucammonium ions per molecule. In a particularly preferred embodiment the o-cresolphthalein mono-phosphoric acid salt contains an average of 2.3 N-methylglucammonium ions per o-cresolphthalein monophosphate molecule.

The mixture according to the invention is also stable towards non-enzymatic hydrolysis in the presence of the sodium or/and magnesium salt necessary for the alkaline phosphatase test as well as in the presence of a buffer substance. In this case the buffer substance is present in such an amount that it ensures a pH value between 10 and 12, preferably between 10 and 11 for the detection of alkaline phosphatase. Possible buffer substances are known to a person skilled in the art. The following are mentioned as examples and not as a final list: carbonates, borates, phosphates, Good buffer substances, glutamate or aspartate. Since the presence of a sodium or/and magnesium salt is advantageous for the determination of alkaline phosphatase, the buffer substance can for example be present in the form of such salts or a sodium or/and magnesium salt can be additionally added to the stable mixture according to the invention.

Preferably, in order to set optimal conditions for the enzyme activity, the mixture according to the invention should contain as a phosphoric acid acceptor at least sufficient N-methylglucamine so that the phosphoric acid which is cleaved from the substrate in the presence of alkaline phosphatase can be captured by the phosphoric acid acceptor. The stable mixture according to the invention preferably contains an excess of N-methyl-glucamine. The molar ratio between enzyme substrate and phosphoric acid acceptor is at least 1:1 but preferably up to 1:4. Of course it is also possible to use ratios that differ from this if optimal enzyme activity conditions are not required.

Although the alkali salt of o-cresolphthalein monophosphoric acid is very unstable towards non-enzymatic hydrolysis, the N-methylglucamine salt is stable towards non-enzymatic hydrolysis even in the presence of very high concentrations of alkali ions.

The mixture according to the invention is very stable in solution. However, it is especially stable towards non-enzymatic hydrolysis in a dry form i.e. as a mixture of the dry individual substances for example also in a lyophilized form. It can also be present in or on a matrix and then be a component of an analytical element for the detection of alkaline phosphatase. Any layer-like material is called a matrix which is able to carry the mixture according to the invention without adversely affecting it. Materials which usually come into consideration as matrix materials are those which are able to take up a solution of the stable mixture according to the invention by swelling or absorption, for example by impregnation, or those which can be coated with the mixture or can be produced in the presence of the mixture according to the invention and incorporate the mixture into the matrix material itself. The latter can for example be accomplished by producing film layers composed of film forming materials in the presence of components of the mixture. Analytical elements are particularly preferred within the scope of the present invention which contain an absorptive porous matrix which is impregnated with a solution of the mixture according to the invention and has been subsequently dried. Paper is used as a particularly preferred matrix material.

The matrix carrying the mixture according to the invention can already be used itself as an analytical element. However, it may also prove to be advantageous to attach the matrix for example to an inert support material which facilitates the handling of the matrix. Similar embodiments are for example known for urine test strips. The matrix containing the stable mixture according to the invention can also be contained in multilayered analytical elements which are known from the state of the art. For example they can be contained in a multilayered analytical element as described in the European Patent Application 0182179 wherein the matrix replaces the spreading and buffer layer of this analytical element.

It has proven to be particularly advantageous for the examination of whole blood to use an analytical element as described for example in the European Patent Application 0461392 in the example of FIG. 1. A transport layer (2) is attached to an inert support foil (5), for example a plastic foil, which serves to transport sample liquid from the sample application zone (7) into the detection zone (8). In principle any material is suitable for the transport layer (2) which is able to transport the liquid to be examined from the sample application zone (7) into the detection zone (8) and in this process does not change it in a way which would impair the analysis. It is particularly advantageous to use a glass fibre fleece as the transport layer (2). A layer (3) for the separation of corpuscular components from the sample liquid is attached to the transport layer (2) and partially covers it. In principle any material can be used for this which enables the separation of corpuscular components from the sample liquid in particular blood cells and above all erythrocytes from blood and does not allow these to reach the detection area (8) in significant amounts so that they do not cause an interference of the detection reaction there. Furthermore the separation layer (3) must not change the sample liquid such that the activity of the alkaline phosphatase to be determined is changed therein and thus falsifies the result. Glass fibre fleeces have proven to be particularly suitable for the separation layer (3) as described for example in the European Patent document 0 045 476. A protective layer (4) is preferably mounted over the separation layer (3) which should prevent damage to the separation layer (3) for example by a pipette during sample application. A net made of inert material such as plastic has proven to be suitable for this. The protective layer (4) and separation layer (3) are attached to the inert support foil (5). This can for example be accomplished by means of a strip of hot-melt adhesive.

At the side of the transport layer (2) a support foil composed of transparent plastic is attached to the matrix (1) which contains the mixture according to the invention. This is preferably achieved by an adhesive site (9) for example a strip of hot-melt adhesive. The matrix (1) is arranged such that it can be brought into contact with the transport layer (2) enabling liquid transition when the transparent support foil is pressed down towards the inert support foil (5).

In order to carry out the method according to the invention for the determination of alkaline phosphatase in a liquid sample, the sample is contacted with a mixture according to the invention whereupon a colour change can be observed when alkaline phosphatase is present. As a rule alkaline phosphatase is detected in body fluids such as blood or samples derived from blood such as plasma or serum. Of course it is also possible to examine other liquids for the presence of alkaline phosphatase. In principle it is possible to add the mixture according to the invention to the sample to be examined or conversely to add the sample to the mixture according to the invention. If the mixture according to the invention is present free of a carrier i.e. as a powder, crystal mixture or in a lyophilized form, it will be advantageous in most cases to add the mixture to the sample to be examined.

If an analytical element according to the invention containing a matrix carrying the mixture according to the invention is used, it is advantageous that the matrix is contacted with the liquid to be examined. For example the matrix is immersed in the liquid to be examined. In a particularly preferred embodiment of the determination of alkaline phosphatase using an analytical element according to the invention whole blood is applied to the protective layer (4) of the particularly preferred analytical element shown in FIG. 1. The blood penetrates into the separation layer (3) and erythrocytes are separated from plasma or serum. The liquid obtained in this manner is sucked by capillary forces into the detection zone (8). Pressure on the support foil with the matrix (1) according to the invention contacts the aqueous phase in the transport layer (2) with the matrix (1), liquid penetrates into the matrix and a determination reaction is triggered. The reaction is observed through the support foil of the matrix (1) by visual means or it is measured by reflection photometry based on the colour change in the matrix (1).

The salt of o-cresolphthalein monophosphoric acid with N-methylglucamine as described as a component of the stable mixture according to the invention is new and is therefore also a subject matter of the present invention. In order to produce it o-cresolphthalein monophosphoric acid is reacted with N-methylglucamine. The production of o-cresolphthalein monophosphoric acid is known to a person skilled in the art from the U.S. Pat. No. 3,975,405. N-methylglucamine is commercially available. D-N-methylglucamine is preferably used.

The reaction of o-cresolphthalein monophosphoric acid with N-methylglucamine is preferably carried out such that o-cresolphthalein monophosphoric acid is dissolved in an organic solvent and admixed with two to four equivalents of N-methylglucamine. The precipitated salt is removed by filtration and purified by recrystallization from a suitable organic solvent. Alcohols such as ethanol and preferably methanol have proven to be suitable for the organic solvent as a reaction medium. Unpolar solvents come into consideration for the recrystallization such as ether. The salt of o-cresolphthalein monophosphoric acid obtained in the above-mentioned manner contains between two and three N-methylglucammonium ions per o-cresolphthalein monophosphoric acid molecule.

The new o-cresolphthalein monophosphoric acid salt according to the invention has proven to be very advantageous for the detection of alkaline phosphatase since the enzymatic cleavage product o-cresolphthalein has a high molar extinction coefficient and thus enables very sensitive determinations.

Since the same organic amine is used as a cation of the enzyme substrate and as a phosphoric acid acceptor, the mixture according to the invention for the alkaline phosphatase test is very simple to produce. Moreover this mixture is very stable towards non-enzymatic hydrolysis. As a consequence such mixtures can be produced without significant amounts of hydrolysis products which leads to low initial signals in measurements and in addition such mixtures are very stable when stored. The presence of alkali ions such as for example sodium ions even in a large excess do not influence the stability of the mixture according to the invention. Since an analytical element according to the invention has a common layer for the enzyme substrate and phosphoric acid acceptor, it is simple to manufacture. Moreover the analytical element according to the invention requires only a small amount of sample liquid because only one layer containing the mixture according to the invention has to take up liquid instead of the recommended two layer form of the state of the art. Furthermore the use of only one layer which already contains a mixture of substrate and acceptor leads to a homogeneous mixture when the sample is applied which leads to reproducible measurement results.

The invention is elucidated in more detail by the following examples.

EXAMPLE 1

Production of o-Cresolphthalein Phosphate N-methyl-glucamine Salt o-Cresolphthalein monophosphoric acid is produced according to the U.S. Pat. No. 3,975,405. 24 g o-cresolphthalein monophosphoric acid is dissolved in 94 ml methanol and 23 g D-N-methylglucamine is added to this. The N-methylglucammonium salt is isolated by precipitation from a ten-fold volume of diethyl ether. The precipitate is dried in a vacuum over sulphuric acid. Yield: 44 g o-cresolphthalein phosphate D-N-methylglucammonium salt.

EXAMPLE 2

Production of o-Cresolphthalein Phosphate Sodium Salt 24 g o-cresolphthalein monophosphoric acid is dissolved in 94 ml methanol, the pH value of the solution is adjusted to 10.5 with NaOH and precipitated in a 10-fold volume with diethyl ether. The precipitate is separated and dried in a vacuum over sulphuric acid.

Yield: 22 g o-cresolphthalein phosphate sodium salt.

EXAMPLE 3

Detection of Alkaline Phosphatase

Paper (long fibre paper, manufacturer Schoeller, Gernsbach, Germany, area weight 12 g/m$^2$) is impregnated with a mixture according to the invention which is produced as follows:

| | |
|---|---|
| water, purified | 500.0 ml |
| sodium hydroxide solution (5N) | 91.0 ml |
| D-N-methylglucamine | 187.4 g |
| L-aspartic acid magnesium salt | 22.0 mg |
| o-cresolphthalein phosphoric acid D-N-methylglucamine salt | 218.1 g | are mixed and subsequently filled up to 1 l with water.

The pH value of the solution is corrected with sodium hydroxide solution (5N) to pH 11.0 if necessary.

After drying the impregnated paper blood serum containing alkaline phosphatase is applied to the paper. A change in colour from yellow to red violet takes place depending on the enzyme activity.

EXAMPLE 4

Comparison of Stability

A paper is produced as described in example 3 containing the mixture according to the invention for the detection of alkaline phosphatase and stored for several weeks at 50° C. After certain time intervals the absorbance at 567 nm is measured against water. Using the o-cresolphthalein monophosphate sodium salt produced in example 2 a mixture for the alkaline phosphatase test is produced according to example 3 instead of the o-cresolphthalein monophosphoric acid N-methylglucammonium salt according to the invention and impregnated on the same long fibre paper and dried so that an analogous analytical element to that described in example 3 is produced. This paper is subjected to the same storage conditions as that containing the methylglucamine salt.

The results after one and a half and three weeks are shown in table 1.

TABLE 1

| Stress period | Absorbance of the paper containing the sodium salt | Absorbance of the paper containing the N-methylglucammonium salt |
|---|---|---|
| 1.5 weeks | 2.664 | 1.022 |
| 3 weeks | 3.735 | 1.255 |

This shows that the sodium salt is much more unstable than the N-methylglucammonium salt towards non-enzymatic hydrolysis.

What is claimed is:

1. A mixture for detection of alkaline phosphatase, comprising
   a N-methyl-glucamine salt of o-cresolphthalein monophosphoric acid; and
   N-methylglucamine.

2. The mixture of claim 1, wherein the N-methylglucamine salt is D-N-methyl-glucamine salt and the N-methylglucamine is D-N-methylglucamine.

3. The mixture of claim 1, wherein the mixture is in a dry form.

4. The mixture of claim 1, wherein the mixture of the salt of and N-methylglucamine is a homogenous mixture.

5. The mixture of claim 1, wherein the N-methylglucamine salt comprises 2 to 3 N-methyl-glucammonium ions per o-cresolphthalein monophosphate molecule.

6. The mixture of claim 1, further comprising a buffer substance.

7. The mixture of claim 6, wherein the buffer substance maintains the pH value of the mixture at values of 10 to 12.

8. The mixture of claim 6, wherein the buffer substance is selected from the group comprising carbonates, borates, and phosphates.

9. The mixture of claim 6, wherein the buffer substance is glutamate or aspartate.

10. The mixture of claim 8, wherein the buffer substance is in the form of a sodium salt.

11. The mixture of claim 8, wherein the buffer substance is in the form of a magnesium salt.

12. The mixture of claim 1, wherein the N-methyl glucamine is present in an amount sufficient to capture phosphoric acid which is cleaved from the N-methyl-glucamine salt of o-cresolphthalein monophosphoric acid in the presence of alkaline phosphatase.

13. The mixture of claim 1, wherein the amount of N-methyl glucamine is greater than the amount of N-methylglucamine salt of o-cresolphthalein monophosphoric acid.

14. The mixture of claim 1, wherein the molar ratio between the N-methyl-glucamine salt of o-cresolphthalein monophosphoric acid and the N-methyl glucamine is about 1:4.

15. An analytical element for determination of alkaline phosphatase in a sample, comprising:
   a matrix having at least one layer, wherein present in or on said layer is a mixture of a N-methyl glucamine salt of o-cresolphthalein monophosphoric acid and a phosphoric acid acceptor; and, wherein in the presence of alkaline phosphatase, said N-methyl glucamine salt of o-cresolphthalein monophosphoric acid changes color.

16. The analytical element of claim 15, wherein the phosphoric acid acceptor is N-methyl-glucamine.

17. The analytical element of claim 15, wherein the matrix is an absorptive porous material.

18. The analytical element of claim 17, wherein the matrix is paper.

19. The analytical element of claim 15, wherein the analytical element further comprises an inert supporting material to which the matrix is attached.

20. A method of detecting alkaline phosphatase in a sample, comprising the steps of
   contacting the sample with a mixture comprising a N-methyl-glucamine salt of o-cresolphthalein monophosphoric acid and N-methylglucamine, to produce a detectable color change signal from reaction of the sample with the mixture when alkaline phosphatase is present in the sample; and
   detecting the color change signal.

21. A method of detecting alkaline phosphatase in a sample, comprising the steps of
   contacting the sample with an analytical element for the detection of an alkaline phosphatase, said element comprising a matrix having at least one layer, wherein present in or on said layer is a mixture of a N-methyl glucamine salt of o-cresolphthalein monophosphoric acid, and a phosphoric acid acceptor, and wherein in the presence of alkaline phosphatase, said N-methyl glucamine salt of o-cresolphthalein monophosphoric acid changes color, to produce a detectable color change signal from reaction of the sample with the mixture when alkaline phosphatase is present in the sample; and
   detecting the color change signal.

22. The method of claim 21, wherein the substrate is an N-methyl-glucamine salt of o-cresolphthalein monophosphoric acid.

23. The method of claim 21, wherein the phosphoric acid acceptor is N-methyl-glucamine.

24. The method of claim 21, wherein the sample is a body fluid.

25. The method of claim 21, wherein the sample is blood or a blood derivative.

26. A N-methylglucamine salt of o-cresolphthalein monophosphoric acid.

27. The salt of claim 26, wherein the salt is a D-N-methylglucamine salt.

28. The salt of claim 26, wherein the salt comprises 2 or 3 N-methyl-glucammonium ions per o-cresolphthalein monophosphate molecule.

29. A process for producing a salt of o-cresolphthalein monophosphoric acid with N-methylglucamine, comprising
   reacting o-cresolphthalein monophosphoric acid with N-methyl-glucamine.

30. The process of claim 29, wherein the reaction is carried out by the following steps:
   dissolving o-cresolphthalein monophospohoric acid in a first organic solvent;
   admixing two to four equivalents of N-methyl-glucamine with the first organic solvent having o-cresolphthalein monophospohoric acid dissolved therein, to form an admixed solution;
   filtering the admixed solution to recover any precipitated salt contained therein; and
   purifying the recovered precipitated salt by recrystallization from a second organic solvent.

31. The process of claim 30, wherein the second organic solvent is the same solvent as the first solvent.

32. The process of claim 30, wherein the second organic solvent is a different solvent than the first solvent.

* * * * *